United States Patent [19]

Ono et al.

[11] 4,081,469
[45] Mar. 28, 1978

[54] PROCESS FOR SEPARATING AND RECOVERING UNREACTED MATERIALS IN UREA SYNTHESIS

[75] Inventors: Hiroshi Ono, Fujisawa; Shigeru Inoue, Kamakura, both of Japan

[73] Assignee: Mitsui Toatsu Chemicals, Tokyo, Japan

[21] Appl. No.: 718,562

[22] Filed: Aug. 30, 1976

[30] Foreign Application Priority Data

Sep. 22, 1975 Japan .................................. 50-113709

[51] Int. Cl.$^2$ ........................................ C07C 126/02
[52] U.S. Cl. ........................................ 260/555 A
[58] Field of Search ............................... 260/555 A

[56] References Cited

U.S. PATENT DOCUMENTS

| | | | |
|---|---|---|---|
| 2,848,493 | 8/1958 | Dewling et al. | 260/555 A |
| 3,049,563 | 8/1962 | Bochinski et al. | 260/555 A |
| 3,876,696 | 4/1975 | Guadalupi et al. | 260/555 A |
| 3,944,605 | 3/1976 | Inoue et al. | 260/555 A |
| 3,984,469 | 10/1976 | Guadalupi et al. | 260/555 A |

*Primary Examiner*—Edward J. Meros
*Attorney, Agent, or Firm*—Fisher, Christen & Sabol

[57] ABSTRACT

Carbon dioxide is reacted with a stoichiometric excess of ammonia at urea synthesis temperatures and pressures in a urea synthesis zone with the mol ratio of ammonia to carbon dioxide being in the range of from 5:1 to 12:1. The urea synthesis effluent from the urea synthesis zone is pressurized to a pressure higher than the urea synthesis pressure, and heated to a temperature higher than the urea synthesis temperature in a separation zone, wherein unreacted ammonium carbamate and excess ammonia contained in said urea synthesis effluent are separated from urea synthesis effluent in the form of a gaseous mixture of ammonia and carbon dioxide. The thus separated gaseous mixture of ammonia and carbon dioxide is recycled to said urea synthesis zone by means of the pressure difference.

15 Claims, 1 Drawing Figure

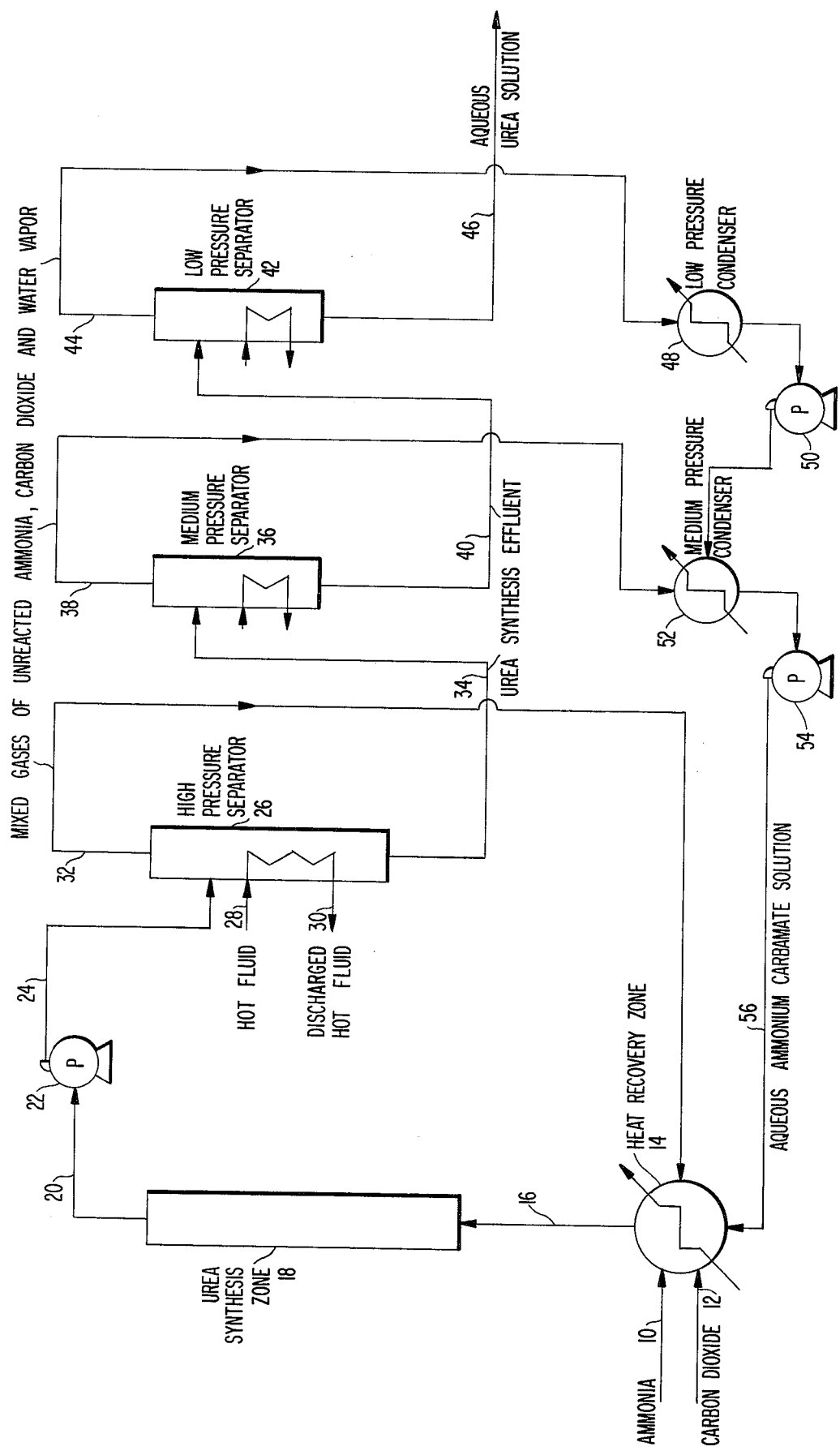

PROCESS FOR SEPARATING AND RECOVERING UNREACTED MATERIALS IN UREA SYNTHESIS

BACKGROUND OF THE INVENTION

1. Field of the Invention

This invention relates to the production of urea from carbon dioxide and ammonia, and more particularly it relates to a process for efficiently separating and recovering unreacted excess ammonia and ammonium carbamate from a urea synthesis effluent.

2. Description of the Prior Art

As is well known in the art, the urea synthesis effluent which is obtained by reacting carbon dioxide with a stoichiometric excess of ammonia under elevated temperature and pressure conditions contains unreacted ammonium carbamate and an excess of ammonia (hereinafter referred to briefly as "unreacted materials") apart from urea and water. In order to effect urea synthesis in an efficient manner, it is necessary to separate these unreacted materials from the urea synthesis effluent and to recycle the thus separated materials to the urea synthesis zone. In general, the unreacted materials can be readily separated by heating the urea synthesis effluent to gasify the unreacted materials. The higher the temperature and the lower the pressure, the separation of the unreacted materials from the urea synthesis effluent is feasible with more ease from the viewpoint of equilibrium. However, when the effluent is heated to too high a temperature, urea tends to be hydrolyzed and the amounts of further impurities such as biuret, etc., are increased. Accordingly, upon separation, the pressure of the urea synthesis effluent is usually reduced and the separation is effected at a low temperature corresponding to the reduced pressure.

In order to recycle the separated unreacted materials comprising the excess ammonia, carbon dioxide and water to the urea synthesis zone, they may be merely compressed and recirculated in gaseous form or they may be condensed to a liquid and recirculated. However, the former method involves several problems such as the requirement of a great deal of power upon compression, mechanical difficulties in compression of the hot and corrosive gas, etc. On the other hand, the latter method is free of the above problems but has its own disadvantage in that the heat released upon condensation of the separated gaseous mixture of unreacted materials cannot be recovered and used effectively since the condensation temperature is low. In addition, when all of the separated unreacted materials are condensed, the condensed liquid is readily separated into two liquid layers, i.e., an ammonia-rich layer and an ammonium carbamate-rich layer, involving some difficulty upon recycling to the urea synthesis zone by means of a pump. In order to avoid this difficulty, it is required that the greater part of the ammonia is separated from the unreacted materials and condensed in an additional condenser for the ammonia.

SUMMARY OF THE INVENTION

It is therefore a primary object of the present invention to provide a process for efficiently recovering the heat energy consumed in recovering the excess of ammonia and unreacted ammonium carbamate from a urea synthesis effluent for recycling to the urea synthesis zone.

It is another object of the present invention to provide a process for recovering excess ammonia and unreacted ammonium carbamate without increasing any impurities in the produced urea.

It is a further object of the present invention to provide a process for separating and recovering excess ammonia and unreacted ammonium carbamate from a urea synthesis effluent for recycling to the urea synthesis zone, with reduced consumption of power and without any mechanical difficulty during the recovery and the recycle.

Still further objects will become apparent from the following detailed description and specific example taken in conjunction with the accompanying drawing which, while indicating preferred embodiments of the present invention, are given by way of illustration only.

In order to attain the above objects, we have made intensive studies of processes for the recovery of unreacted materials from the urea synthesis effluent from a urea synthesis zone and it has been found that when the urea synthesis is conducted under conditions of an ammonia:carbon dioxide mol ratio above 5:1, the amount of biuret impurity in the produced urea is hardly increased, if at all, in amount even if the urea effluent is heated to a temperature slightly higher than the oridinary urea synthesis temperature. In general, the heating of the urea synthesis effluent to such a higher temperature has been avoided as much as possible by the prior art since urea tends to be converted to biuret by such heating. Furthermore, it has been found that when the urea synthesis is effected by using a large excess of ammonia, the equilibrium partial pressure of ammonia increases sharply even with a slight increase in temperature in the vicinity of the urea synthesis temperature and pressure conditions. This can be applied to separation of the excess ammonia from the urea synthesis effluent by merely heating the reaction mixture to a temperature slightly higher than the temperature of that in the urea synthesis zone without reducing the pressure of the urea synthesis zone, i.e., under a pressure equal to or slightly higher than the pressure of the urea synthesis zone. The present invention is based on the above findings, leading to a process for recovering unreacted materials from a urea synthesis effluent as will be hereinafter described in detail.

BRIEF DESCRIPTION OF THE DRAWING

The sole FIGURE is a flow chart showing the production of a urea synthesis effluent and the treatment of unreacted ammonium carbamate and excess ammonia contained therein in accordance with the process of the present invention.

DESCRIPTION OF THE PREFERRED EMBODIMENTS

According to the present invention, there is provided a process for treating unreacted ammonium carbamate and excess ammonia contained in a urea synthesis effluent which comprises reacting in a urea synthesis zone carbon dioxide with a stoichiometric excess of ammonia at urea synthesis pressures and temperature to form said urea synthesis effluent, the mol ratio of said ammonia to said carbon dioxide being in the range of from 5:1 to 12:1, pressurizing said urea synthesis effluent to a pressure higher than said urea synthesis pressure, heating to a temperature higher than said urea synthesis temperature said pressurized urea synthesis effluent in a separation zone to separate therefrom said unreacted ammonium carbamate and said excess ammonia in the form of a mixed gas of ammonia and carbon dioxide, and recycling said mixed gas having the pressure higher than said urea synthesis pressure to said urea synthesis zone. According to the process of the invention, most of the excess ammonia and portions of the carbon dioxide and water can be separated suitably from the urea synthesis effluent without use of any stripping agent such as carbon dioxide, ammonia or other inert gas, merely by heating the urea synthesis effluent pressurized to a pressure slightly higher than the urea synthesis pressure. In this connection, the hydrolysis of urea and formation of impurities such as biuret, etc., which have been heretofore believed to unavoidably occur upon heating the urea synthesis effluent are found to take place only in a negligible extent so long as the effluent is heated up to such a temperature as required to practice the invention. When the recovery process of the invention is conducted especially in a highly excessive ammonia atmosphere, the rates of hydrolysis with those in urea synthesis processes using known excess ammonia-recovering techniques.

In the practice of the present invention, the excess ammonia separated together with small amounts of carbon dioxide and water under a pressure slightly higher than the pressure in the urea synthesis zone can be recirculated to the urea synthesis zone as such by use of the pressure difference, without use of any additional means for the recycle of the ammonia. In other words, the power required for recycling the excess ammonia is only that required to pressurize the urea synthesis solution up to a pressure in the separation zone wherein the unreacted materials are separated from the urea synthesis effluent. This results in a remarkable reduction in power cost as compared with the case of compressing the separated mixed gas for recirculation. In the process of the present invention, the separated excess ammonia and other components are recycled to the urea synthesis zone in the form of a hot mixed gas, so that the quantity of heat required for separation of unreacted materials is recoverable in the urea synthesis zone at a high temperature level, reducing the heat energy needed for the urea synthesis to a considerable extent.

The pressure in the separation zone for separating the unreacted materials from the urea synthesis effluent should be higher than the pressure in the urea synthesis zone by a degree sufficient to allow smooth feedback to the unreacted materials to the urea synthesis zone by this pressure difference alone. Any pump means such as of a centrifugal type and a reciprocating type may be used in order to pressurize the urea synthesis effluent up to the separation pressure so long as they are unaffected by the high pressure and the high temperature of the separation zone. Instead of using these pumps, the urea synthesis effluent may be pressurized by means of an ejector means using a power source pressurized and hot liquid ammonia which is obtained by pressurizing a part or all of liquid ammonia to be fed to the urea synthesis zone to a pressure higher than the pressure in the separation zone and heating the thus pressurized liquid ammonia by indirect heat exchange with said hot mixed gas of unreacted materials separated in the separation zone. All of the liquid ammonia mixed with the urea synthesis effluent is also substantially separated together with the unreacted excess ammonia in the separation zone and introduced into the urea synthesis zone. The amount of heat required for separating the liquid ammonia mixed with the urea synthesis effluent in the ejector from the urea synthesis effluent in the separation zone is equal to the sum of the amount of heat generated upon mixing with the urea synthesis effluent in the ejector and of the latent heat of vaporization of the ammonia. This produces the same result as the case where liquid ammonia is directly fed to the urea synthesis zone, from the viewpoint of heat balance.

In practicing the process of the invention, it is important to suitably select the ratio of ammonia to carbon dioxide in the urea synthesis zone. When the ammonia:carbon dioxide mol ratio is below 5:1, the hydrolysis of urea and formation of biuret unfavorably take place to a considerable extent upon heating the urea synthesis solution in the separation zone for separating the unreacted materials from the solution. In contrast, too much of an excess of ammonia is also unfavorably since the amount of ammonia to be recovered and recycled increases correspondingly, with an increased amount of heat and power being required for the recovery and recycle operations. Accordingly, the ammonia:carbon dioxide mol ratio in the urea synthesis zone is preferred to be in the range of 5:1–12:1 . The amounts of urea and ammonium carbamate in the urea synthesis zone are also taken into account for calculation of said mol ratio by way of reducing one of urea or ammonium carbamate to 2 mols of ammonia and 1 mol of carbon dioxide.

As described hereinbefore, the pressure in the separation zone is sufficient if it is higher than that of the urea synthesis zone so that the unreacted materials separated in the separation zone can be recycled in the form of gases to the urea synthesis zone using only the difference in pressure between the separation zone and the urea synthesis zone. The separation pressure is preferably from 0.1 to 5 kg/cm$^2$ higher than the pressure in the urea synthesis zone. At the same time, the separation zone should be operated in such a temperature range whereby said separation of most of the excess ammonia is satisfactorily achieved under the above-defined pressure and the hydrolysis of urea and formation of biuret are still negliglible. The separation zone is preferably operated at temperatures from 50° to 35° C. higher than the temperature of the urea synthesis zone. That is, a temperature of from 185° to 235° C. is preferably used.

The gaseous ammonia separated in the separation zone according to the process of the invention contains from 0.5 to 10 mol % of carbon dioxide and from 1 to 20 mol % of water vapor. If a rectification tower-type separator is used for the separation, the water vapor content may be reduced to from about 0.5 to 10 mol %.

The heat which is employed for separation and recovery of the excess ammonia may be recovered by any known methods which ensure the recovery, in the form of hot water or steam, of substantially all of the surplus heat existing in the synthesis zone. For example, there are generally used a method wherein the separated and recovered gas containing ammonia and carbon dioxide is passed through a heat exchanger prior to being recycled to the urea synthesis zone, a method using a heat exchanger provided in the urea synthesis zone whereby to cool the urea synthesis zone and at the same time to recover the heat in the form of steam, and other like methods. Alternatively, the hot gas separated in the separation zone containing the ammonia and carbon dioxide may be passed through a heat exchanger disposed in a step requiring heating, such as the step of concentrating an aqueous urea solution whereby to recover the heat of the hot gas. When the mixed gas of unreacted materials separated from the urea synthesis effluent is cooled by indirect heat exchange prior to being recycled to the urea synthesis zone, part of the mixed gas is condensed and the condensate is recycled to the urea synthesis zone together with the mixed gas.

In the urea synthesis process, it is unavoidable that highly corrosive and hot ammonium carbamate will be treated. There has been made an extensive study on the development of materials for equipment and also on the development of corrosion-preventing techniques. To prevent this corrosion is still a problem to be solved. Urea synthesis generally involves an increased cost for equipment investment so as to prevent corrosion or a reduction in rate of operation due to various corrosion problems. However, the process of the present invention has an advantage over known processes in that the synthesis of urea and the separation of the unreacted materials are effected in a highly excessive ammonia atmosphere so that the corrosion of equipment is reduced to a certain extent, making it possible to use a more inexpensive material for equipment than those employed in conventional processes.

The present invention will be even more clearly understood from the following description with reference to the accompanying illustrative and non-limiting drawing.

In the drawing, starting ammonia and carbon dioxide are charged into heat recovery zone 14 through lines 10 and 12, respectively. Heat recovery zone 14 is operated under a pressure of 0.1 kg/cm$^2$ or more higher than that of urea synthesis zone 18 and at a urea synthesis temperature. In heat recovery zone 14, the starting ammonia and carbon dioxide are reacted with each other to form ammonium carbamate during which heat of formation is generated and a portion of this heat is used for operation of urea synthesis zone 18, the other portion being recovered in the form of steam. Heat recovery zone 14 is connected through line 16 with urea synthesis zone 18 which is operated at a temperature of from 180° to 210° C. under a pressure of from 150 to 260 kg/cm$^2$. The urea synthesis effluent from urea synthesis zone 18 is passed from the outlet thereof through line 20 to pump 22 wherein its pressure is increased by 0.2 kg/cm$^2$ or more. As discussed hereinabove, instead of using pumps, the urea synthesis effluent may be pressurized by means of an ejector means. For example, pump 22 may be substituted by an ejector means driven by pressurized and heated liquid ammonia. The thus pressurized solution is fed to high pressure separator 26 through line 24. High pressure separator 26 is operated at a pressure of 0.1 kg/cm$^2$ or more higher than that of heat recovery zone 14 and is heated with a hot fluid charged from line 28 and discharged from line 30. The unreacted materials are separated in high pressure separator 26 from the urea synthesis effluent in the form of a mixed gas of ammonia, carbon dioxide and water vapor, and fed to heat recovery zone 14 through line 32. At the same time, the urea synthesis effluent from which the unreacted materials have been separated is fed through line 34 to a subsequent medium pressure separator 36 and to low pressure separator 42 for separating small amounts of remaining unreacted materials therefrom, and is finally withdrawn from line 46 in the form of an aqueous urea solution containing only traces if any of unreacted materials. That is, in medium pressure separator 36 which is operated at a temperature of from 140° to 170° C. and under a guage pressure of from 14 to 18 kg/cm$^2$, 90% of the unreacted materials are separated from the urea synthesis effluent and discharged from line 38 in the form of a mixed gas of carbon dioxide, ammonia and water vapor. The urea synthesis effluent from which the unreacted materials have been thus separated is then fed through line 40 to low pressure separator 42 in which substantially all of the unreacted materials are separated from the urea synthesis effluent. The resulting aqueous urea solution is withdrawn from line 46. Low pressure separator 42 is operated at a temperature of from 110° to 145° C. and under a gauge pressure of from 0.05 to 3.5 kg/cm$^2$, whereby the mixed gas of carbon dioxide, ammonia and water vapor is separated as described above. The mixed gas separated in the low pressure separator is then fed through line 44 to low pressure condenser 48 in which the gas is cooled to from 30° to 60° C. for condensation to form an aqueous ammonium carbamate-containing solution. This aqueous solution is pressurized and fed to medium pressure condenser 52 by means of pump 50. In the medium pressure condenser 52, the mixed gas fed from line 38 and composed of carbon dioxide, ammonia and water vapor is allowed to be absorbed in the aqueous solution at a temperature of from 50° to 120° C. The resulting solution is then fed back to heat recovery zone 14 through line 56 by means of pump 54.

The present invention will be particularly illustrated by way of the following non-limiting example.

EXAMPLE

Ammonia and carbon dioxide were fed to heat recovery zone 14 through lines 10 and 12 at feed rates of 56.8 tons/day and 74.0 tons/day, respectively, and further fed through line 16 to urea synthesis zone 18 together with unreacted materials from lines 32 and 56. Urea synthesis zone 18 was operated at 185° C. and under a pressure of 180 kg/cm$^2$. The urea synthesis effluent from urea synthesis zone 18 has a composition, in parts by weight, of 102.1 parts of urea, 43.4 parts of ammonium carbamate, 117.1 parts of ammonia, 47.1 parts of water and 0.4 part of biuret. The urea synthesis effluent was fed through line 20 to pump 22 wherein its pressure was raised to 183 kg/cm$^2$. Then, the effluent was fed to high pressure separator 26 through line 24.

High pressure separator 26 was operated at a temperature of 195° C. under a pressure of 183 kg/cm$^2$, in which 107.2 tons/day of ammonia, 6.7 tons/day of carbon dioxide and 5.5 tons/day of water were separated from the urea synthesis effluent and recycled to heat recovery zone 14 through line 32. Separator 26 was kept hot by means of 20 kg/cm$^2$ of steam. The urea synthesis effluent from the bottom of high pressure separator 26 had a composition, in parts by weight, of 100.4 parts of urea, 33.5 parts of ammonium carbamate, 14.9 parts of ammonia, 41.2 parts of water and 0.6 part of biuret. This urea synthesis effluent was charged into medium pressure separator 36 operated under pressure and temperature conditions of 18 kg/cm$^2$ and 170° C. to separate most of the remaining unreacted materials therefrom, followed by being fed to low pressure separator 42 operated under pressure and temperature conditions of 0.5 kg/cm$^2$ and 140° C. to separate substantially all of the residual unreacted materials. The resulting aqueous 76% urea solution was withdrawn from line 46. At the same time, the separated unreacted materials were condensed in low pressure condenser 48 and further in medium pressure condenser 52, which was recycled through line 56 to heat recovery zone 14 in the form of an aqueous solution having a composition, in parts by weight, of 33.7 parts of ammonium carbamate, 15.4 parts of ammonia, and 10.8 parts of water.

What is claimed is:

1. A process for treating unreacted ammonium carbamate and excess ammonia contained in a urea synthesis effluent which comprises reacting in a urea synthesis zone carbon dioxide with a stoichiometric excess of ammonia at urea synthesis pressures and temperatures to form said urea synthesis effluent, the mol ratio of said ammonia to said carbon dioxide being in the same range of 5:1 to 12:1, pressurizing said urea synthesis effluent from said urea synthesis zone to a pressure higher than said urea synthesis pressure, heating to a temperature higher than said urea synthesis temperature said pressurized urea synthesis effluent in a separation zone to separate therefrom said unreacted ammonium carbamate and said excess ammonia in the form of a mixed gas of ammonia and carbon dioxide, and recycling said mixed gas having the pressure higher than said urea synthesis pressure to said urea synthesis zone.

2. The process as claimed in claim 1 wherein said separation zone is operated under a pressure of from about 0.1 to 5 kg/cm$^2$ higher than the pressure in said urea synthesis zone.

3. The process as claimed in claim 1 wherein said separation zone is operated at a temperature of from about 5° to 35° C. higher than the temperature in the urea synthesis zone.

4. The process as claimed in claim 1 wherein said mixed gas is separated from said urea synthesis effluent by rectification in said separation zone.

5. The process as claimed in claim 1 wherein said urea synthesis effluent from said urea synthesis zone is pressurized by means of a reciprocating pump means.

6. The process as claimed in claim 1 wherein said urea synthesis effluent from said urea synthesis zone is pressurized by means of a centrifugal pump means.

7. The process as claimed in claim 1 wherein said urea synthesis effluent from said urea synthesis zone is pressurized by means of an ejector means driven by liquid ammonia which is pressurized to a pressure higher than that of said separation zone and then heated.

8. The process as claimed in claim 7 wherein said liquid ammonia used to drive said ejector means and mixed with said urea synthesis effluent in said ejector means is substantially separated together with said unreacted ammonium carbamate and excess ammonia from said urea synthesis effluent and recycled to the urea synthesis zone.

9. The process as claimed in claim 1 wherein at least a part of said mixed gas of ammonia and carbon dioxide is condensed by indirectly cooling with a coolant and the resulting condensate is recycled to said urea synthesis zone.

10. The process as claimed in claim 9 wherein said condensate is recycled together with the uncondensed part of said mixed gas.

11. The process as claimed in claim 9 wherein said coolant is an aqueous urea solution to be concentrated.

12. The process as claimed in claim 9 wherein said coolant is the pressurized liquid ammonia to be fed through an ejector for pressurizing said urea synthesis effluent from said urea synthesis zone.

13. The process as claimed in claim 1 wherein said recovered mixed gas of ammonia and carbon dioxide and make-up carbon dioxide and liquid ammonia are reacted in a heat recovery zone to form ammonium carbamate while removing the surplus heat of reaction by indirect heat exchange with water for generating steam and said formed ammonium carbamate is fed to said urea synthesis zone.

14. The process as claimed in claim 1 wherein said urea synthesis effluent, from which said excess ammonia and said unreacted ammonium carbamate have been separated, is subjected to a medium pressure separation stage and finally to a low pressure separation stage, thereby separating in each stage the still remaining unreacted ammonium carbamate from said urea synthesis effluent in the form of a mixed gas of ammonia and carbon dioxide, said mixed gases from at least said medium pressure separation stage being absorbed in an absorbent selected from the group consisting of water, aqueous ammonia, aqueous urea, aqueous ammonium carbamate and an aqueous solution containing urea and ammonium carbamate to form an ammonium carbamate containing solution, and the resultant recovered aqueous ammonium carbamate solution is recycled to said urea synthesis zone.

15. The process as claimed in claim 14 wherein said recovered mixed gas of ammonia and carbon dioxide, make-up carbon dioxide and recovered aqueous ammonium carbamate solution are reacted in a heat recovery zone to form ammonium carbamate while removing the surplus heat of reaction by indirect heat exchange with water for generating steam and said formed ammonium carbamate is fed to said urea synthesis zone.

* * * * *